United States Patent

Hamby et al.

[11] Patent Number: 5,730,849
[45] Date of Patent: Mar. 24, 1998

[54] HIGH SENSITIVITY DYES AS STAINS FOR RNA BANDS IN DENATURING GELS

[75] Inventors: R. Keith Hamby, Albany; Layne Huiet, Davis, both of Calif.

[73] Assignee: Bio-Rad Laboratories, Inc., Hercules, Calif.

[21] Appl. No.: 723,053

[22] Filed: Sep. 30, 1996

[51] Int. Cl.$^6$ .................................................. G01N 27/26
[52] U.S. Cl. .................................... 204/461; 204/452
[58] Field of Search ........................... 204/452, 461, 204/603, 612, 456, 451

[56] References Cited

U.S. PATENT DOCUMENTS

| 5,312,921 | 5/1994 | Glazer et al. | 546/108 |
| 5,437,980 | 8/1995 | Haugland | 435/6 |
| 5,582,984 | 12/1996 | Bieniarz et al. | 435/6 |

OTHER PUBLICATIONS

S.C. Benson, et al., "Heterodimeric DNA–Binding Dyes Designed for Energy Transfer: Stability and Applications of the DNA Complexes," *Nucleic Acids Research* (1993) 21(24):5720–5726.

S.C. Benson, et al., "Heterodimeric DNA–Binding Dyes Designed for Energy Transfer: Synthesis and Spectroscopic Properties," *Nucleic Acids Research* (1993) 21(24):5727–5735.

CAplus abstaract of Gruendemann et al. ("Ethidium bromide staining during denaturation with glyoxal for sensitive detection of RNA in agarose gel electrophoresis", Anal. Biochem. (1994), 216 (2), 459–61), No month available., 1994.

CAplus abstract of Zhiyuan Gong ("Improved RNBA staining in formalehyde gels", Biotechniques (1992), 12(1), 74, 76), No month available., 1992.

*Primary Examiner*—Kathryn L. Gorgos
*Assistant Examiner*—Alex Naguerola
*Attorney, Agent, or Firm*—Townsend and Townsend and Crew LLP

[57] ABSTRACT

The visualization of RNA bands in denaturing electrophoresis gels is improved by staining the gels with a 2,7-diamino-10-(N,N,N',N'-tetramethyl-1,3-propanediamino)-propyl-9-phenylphenanthridine dihalide hydrohalide or a 2,7-diamino-10-[3-(diethylmethylammonio)propyl]-9-phenylphenanthridine dihalide. These dyes provide effective contrast for sensitive detection without the need for extensive washing of excess dye from the gels to lower background noise.

13 Claims, No Drawings

HIGH SENSITIVITY DYES AS STAINS FOR RNA BANDS IN DENATURING GELS

BACKGROUND OF THE INVENTION

1. Field of the Invention

This invention lies in the field of gel electrophoresis of nucleic acid, and particularly the staining of gels to visualize RNA.

2. Description of the Prior Art

A variety of procedures in nucleic acid studies rely on the fractionation of nucleic acids by gel electrophoresis, and the visualization of the resulting bands by staining the gels with dyes. The dye of choice is generally the fluorescent dye ethidium bromide, which offers sensitivity and a relatively low level of background fluorescence. DNA studies are performed by first separating the sample into bands on an appropriate gel, then staining the gel by immersion in a solution of the stain for approximately thirty minutes, followed by rinsing the gel for an additional thirty minutes to remove background stain that is not associated with the DNA.

RNA separations present a problem, however, since the RNA fragments are generally single stranded. Molecular weight determinations of RNA therefore require that the separations be run in the presence of denaturing agents, prominent examples of which are formaldehyde and glyoxal. When formaldehyde is used, it is generally incorporated into the gel during the preparation of the gel and also added to the sample. The formaldehyde causes the entire gel to fluoresce when stained with the ethidium bromide or other conventional dyes, thereby lowering the sensitivity of the dye and making it difficult or impossible to distinguish the bands. To avoid this, either the formaldehyde must be removed from the gels by scrupulous rinsing prior to application of the stain, or the gel must rinsed for 1 to 2 hours after the staining procedure. When glyoxal is used, it is generally added only to the sample, and acridine orange is preferred over ethidium bromide as the dye. Like ethidium bromide in formaldehyde gels, acridine orange in glyoxal gels causes background fluorescence that results in low sensitivity, and prolonged destaining is required here as well. These destaining steps are time-consuming and generate waste materials that require disposal, thereby detracting from the efficiency of the procedure as a whole.

SUMMARY OF THE INVENTION

It has now been discovered that certain dyes can be used with denaturing gels in RNA separations to provide higher sensitivity from the dyes themselves and to yield well-defined and readily distinguishable bands without the need for extensive washing either to remove the denaturing agent before the stain is applied or to remove excess stain after the stain is applied. These dyes include 2,7-diamino-10-(N,N,N',N'-tetramethyl-1,3-propanediamino)propyl-9-phenylphenanthridine dihalide hydrohalides and 2,7-diamino-10-[3-(diethylmethylammonio)propyl]-9-phenylphenanthridine dihalides, both of which are heretofore known for use in microscopy and flow cytometry, but not in gels.

DETAILED DESCRIPTION OF THE INVENTION AND PREFERRED EMBODIMENTS

The 2,7-diamino-10-(N,N,N',N'-tetramethyl-1,3-propanediamino)propyl-9-phenylphenanthridine dihalide hydrohalides used in this invention have the formula

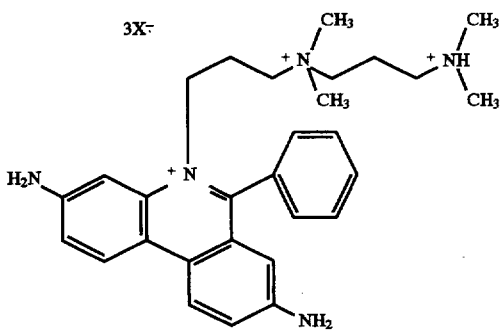

The symbol X in this formula and the formula below denotes a halogen atom. Of these, the preferred compound is that in which X is Cl. The 2,7-diamino-10-[3-(diethylmethylammonio)propyl]-9-phenylphenanthridine dihalides used in this invention have the formula

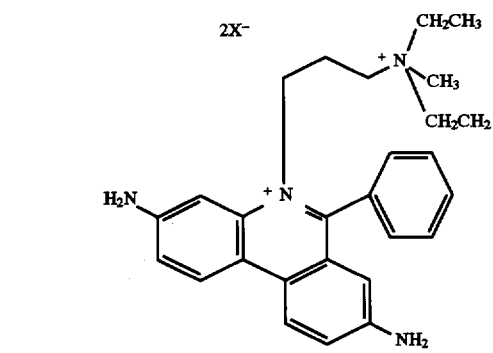

Of these, the preferred compound is that in which X is I. This compound is known by its common name propidium iodide.

These dyes are used at concentrations that are typical for dyes of the prior art. Actual concentrations are not critical to this invention and can vary. In practical use, typical concentrations will fall within the range of about 0.2 µg/mL to about 1.5 µg/mL (micrograms of dye per milliliter of dye solution), while a preferred range is from about 0.5 µg/mL to about 1.0 µg/mL.

The denaturing agent is used in a denaturing amount. The term "denaturing amount" is used herein to denote a concentration or amount of denaturing agent that will denature substantially all of the RNA in the sample. When glyoxal is used as the denaturing agent, it is included in the sample to be applied to the gel. The concentration needed for denaturation can vary. Typical concentrations fall within the range of about 0.01M to about 2.0M, although the most common concentrations are 1.0M of concentrations close to this amount. Likewise, formaldehyde can be included in the sample at concentrations that are not critical, typical concentrations ranging from about 1.1M to about 2.2M. Formaldehyde is usually used in combination with formamide, at concentrations well known to those skilled in the art. When formaldehyde is incorporated into the gel, the concentration is likewise noncritical and can vary. Typical concentrations in the gel formulation are from about 0.3M to about 10.0M, with preferred concentrations ranging from about 1.0M to about 5.0M.

While this invention is applicable to electrophoresis gels in general, polyacrylamide and agarose gels are preferred, and agarose gels are particularly preferred. Electrophoresis can be performed in any conventional gel configuration, including slab gels, tube gels and gels in capillaries. When slab gels are used, they can be either horizontally arranged gels or vertically arranged gels.

The dye is best applied to the gel after the separation has been performed, by immersing the gel in the dye and allowing the gel to incubate with the dye for a period of time ranging from a few minutes to several hours. A period of time ranging from about fifteen minutes to one hour will generally suffice.

The benefits of this invention will be obtained by applying the dye and detecting the bands without any intervening washing (or rinsing) steps to eliminate dye not associated with the RNA. The benefits of the invention will also be obtained by including a washing step after application of the dye. When a wash step is included, the dyes of this invention provide favorable results with a relatively short wash step. Thus, a wash of one minute duration or less is adequate in these circumstances.

Detection of the bands can be performed by any conventional method for fluorescent dyes. Irradiation of the gel for excitation will generally be performed at a wavelength chosen to be within a major absorption band of the dye, and may therefore vary with the selection of the dye. Scanning systems can be employed.

The following examples are offered for illustrative purposes only.

EXAMPLE 1

This example compares one of the stains in accordance with this invention with ethidium bromide in a formaldehyde gel.

A stock solution containing 20 ng/mL of RNA was prepared by mixing 1.2 µL of undiluted single stranded synthetic marker RNA (at 200 ng/µL) with 10.8 µL of a buffer solution prepared by mixing 250 µL formamide, 83 µL formaldehyde and 50 µL 10×2-(N-morpholino) propanesulfonic acid (MOPS). Nine tubes were each charged with 9 µL of the buffer solution, and sufficient buffer was then removed from each tube and replaced with either the 200 ng/µL RNA solution or the 20 ng/µL RNA solution to produce a series of dilutions. An additional 3.5 volumes (31.5 µL) of buffer was then added to each tube, and the tube contents were heated to 65° C. for ten minutes, followed immediately by chilling in ice water. To each tube were then added 4.5 µL of loading buffer, which consisted of 50% glycerol, 0.5×MOPS, 0.25% bromophenol blue, the latter to serve as a marker dye.

Two electrophoresis slab gels were prepared, each containing 1% (by weight) agarose in 1×MOPS and 2.2M formaldehyde. Samples 20 µL each in volume from each tube were loaded onto each of the two gels in separate lanes, such that the eight lanes of each gel contained RNA loadings of 800 ng, 400 ng, 200 ng, 100 ng, 50 ng, 25 ng, 12.5 ng, and 6.25 ng, respectively. The running buffer for each gel was 1×MOPS diluted with diethylpyrocarbonate-treated water, and the gels were run at a constant 75 V until the marker dye had migrated two-thirds of the way down the gel. One gel was then stained by immersion in 100 mL of fresh 1×MOPS containing ethidium bromide at a concentration of 0.3 µg/mL, and the other was stained in the same manner except that 2,7-diamino-10-(N,N,N',N'-tetramethyl-1,3-propanediamino)propyl-9-phenylphenanthridine dichloride hydrochloride at a concentration of 2 µg/mL was substituted for the ethidium bromide. In the first gel, staining with ethidium bromide was maintained for 20 minutes, followed by destaining (washing) for ten minutes. In the second gel, staining with 2,7-diamino-10-(N,N,N',N'-tetramethyl-1,3-propanediamino)propyl-9-phenylphenanthridine dichloride hydrochloride was maintained for thirty minutes, with no subsequent washing.

Both gels were then imaged by transillumination at 302 nm. The ethidium bromide gel failed to show distinct bands for the various RNA fractions, whereas the bands in the 2,7-diamino-10-(N,N,N',N'-tetramethyl-1,3-propanediamino)propyl-9-phenylphenanthridine dichloride hydrochloride gel were sharply defined and readily distinguishable.

EXAMPLE 2

This example again compares a stain in accordance with this invention with ethidium bromide, this time in a glyoxal gel.

Sample solutions were formed by first dissolving single-strand synthetic marker RNA in a solution of 1M glyoxal in 50% aqueous dimethyl sulfoxide, and then diluting the solution in 20 mM N-2-hydroxyethylpiperazine-N'-2-ethanesulfonic acid/-ethylenediaminetetraacetic acid (HEPES/EDTA) containing a marker dye. Each dilution was heated at 52° C. for one hour, followed by cooling on ice.

The gels used were 1% agarose in 20 mM HEPES/EDTA buffer, and samples of appropriate size were loaded in each lane to achieve loadings of 4 µg, 2 µg, 1 µg, 0.5 µg, 0.25 µg and 0.125 µg per lane. Electrophoresis was performed at 80 volts for approximately 1.5 hours as the marker dye had migrated one-half to two-thirds the length of the gel.

One gel was then stained with 50 mL of 1×HEPES buffer containing ethidium bromide at 0.3 µg/mL, and the other gel with 50 mL of 1×HEPES buffer containing 2,7-diamino-10-(N,N,N',N'-tetramethyl-1,3-propanediamino)propyl-9-phenylphenanthridine dichloride hydrochloride at 0.8 µg/mL, followed in each case by photographing the gels without destaining. Visual observation of the photographs indicated that on the gel stained with ethidium bromide, only the first three lanes (starting with the highest loading) were visible, and these only faintly so, whereas on the gel stained with the 2,7-diamino-10-(N,N,N',N'-tetramethyl-1,3-propanediamino)propyl-9-phenylphenanthridine dichloride hydrochloride, all six lanes were clearly visible. The gels were then destained for thirty minutes by rinsing in the same buffer without the dyes, and reexamined. A comparison between the gels after destaining with the same gels prior to destaining showed no difference in the number of visible bands or the contrast as a result of the destaining.

EXAMPLE 3

This example illustrates the use of two stains in accordance with this invention, applied independently—2,7-diamino-10-(N,N,N',N'-tetramethyl-1,3-propanediamino) propyl-9-phenylphenanthridine dichloride hydrochloride and propidium iodide.

The gels used in these tests were 1% agarose in 1×MOPS buffer with 6% (2.2M) formaldehyde. The RNA used was *E. Coli* ribosomal RNA, and samples were prepared in six successive dilutions, followed by heating each sample in a solution of the marker dye, buffer, formaldehyde and formamide for ten minutes at 65° C. as in Example 1 to denature the RNA before loading the samples onto the gels. Samples of appropriate size were loaded in each lane to achieve loadings ranging from 4 µg to 0.125 µg RNA per lane. Electrophoresis was performed at 80 volts for approximately 1.5 hours until the marker dye had migrated one-half to two-thirds the length of the gel.

One gel was then stained in 50 mL of 1×MOPS buffer containing 0.8 μg/mL of 2,7-diamino-10-(N,N,N',N'-tetramethyl-1,3-propanediamino)propyl-9-phenylphenanthridine dichloride hydrochloride. The other gel was stained in 50 mL of 1×MOPS buffer containing 1 μg/mL propidium iodide. Staining was performed at room temperature by gentle agitation of the gels in the stains for 40 minutes, with no subsequent rinsing. Visual observation of the resulting gels showed distinct bands in the propidium iodide-stained gel through four of the six dilutions, and distinct bands in the 2,7-diamino-10-(N,N,N',N'-tetramethyl-1,3-propanediamino)propyl-9-phenylphenanthridine dichloride hydrochloride-stained gel through all six dilutions.

The foregoing is offered primarily for purposes of illustration. It will be readily apparent to those skilled in the art that the concentrations, additional system components, gels, staining techniques, and other parameters of the invention and the procedures in which the invention can be used can be further modified or substituted in various ways without departing from the spirit and scope of the invention.

We claim:

1. A method for detecting single stranded RNA in a denaturing electrophoresis gel, said method comprising staining said RNA with a dye comprising a member selected from the group consisting of a 2,7-diamino-10-(N,N,N',N'-tetramethyl-1,3-propanediamino)propyl-9-phenylphenanthridine dihalide hydrohalide and 2,7-diamino-10-[3-(diethylmethylammonio)propyl]-9-phenylphenanthridine dihalide, and detecting said dye in separated bands of said RNA in said gel.

2. A method in accordance with claim 1 in which said gel contains a denaturing amount of glyoxal.

3. A method in accordance with claim 1 in which said gel contains a denaturing amount of formaldehyde.

4. A method in accordance with claim 1 in which said gel is an agarose gel.

5. A method in accordance with claim 1 comprising staining said RNA by staining said gel subsequent to electrophoresis of said RNA therein, and detecting said single stranded RNA subsequent to staining said gel without an intervening rinse of said gel or with an intervening rinse of no more than approximately one minute in duration.

6. A method in accordance with claim 1 comprising staining said RNA by staining said gel subsequent to electrophoresis of said RNA therein, and detecting said single stranded RNA subsequent to staining said gel but without an intervening rinsing of said gel.

7. A method in accordance with claim 1 comprising staining said gel with a 2,7-diamino-10-(N,N,N',N'-tetramethyl-1,3-propanediamino)propyl-9-phenylphenanthridine dihalide hydrohalide.

8. A method in accordance with claim 7 in which said 2,7-diamino-10-(N,N,N',N'-tetramethyl-1,3-propanediamino)propyl-9-phenylphenanthridine dihalide hydrohalide is 2,7-diamino-10-(N,N,N',N'-tetramethyl-1,3-propanediamino)propyl-9-phenylphenanthridine dichloride hydrochloride.

9. A method in accordance with claim 1 in which said gel contains a denaturing amount of glyoxal, said method comprising staining said gel with 2,7-diamino-10-(N,N,N',N'-tetramethyl-1,3-propanediamino)propyl-9-phenylphenanthridine dichloride hydrochloride.

10. A method in accordance with claim 1 in which said gel contains a denaturing amount of formaldehyde, said method comprising staining said gel with 2,7-diamino-10-(N,N,N',N'-tetramethyl-1,3-propanediamino)propyl-9-phenylphenanthridine dichloride hydrochloride.

11. A method in accordance with claim 1 in which said gel contains a denaturing amount of glyoxal, said method comprising staining said gel with a 2,7-diamino-10-[3-(diethylmethylammonio)propyl]-9-phenylphenanthridine dihalide.

12. A method in accordance with claim 11 in which said 2,7-diamino-10-[3-(diethylmethylammonio)propyl]-9-phenylphenanthridine dihalide is 2,7-diamino-10-[3-(diethylmethylammonio)propyl]-9-phenylphenanthridine diiodide.

13. A method in accordance with claim 1 in which said gel contains a denaturing amount of formaldehyde, said method comprising staining said gel with 2,7-diamino-10-[3-(diethylmethylammonio)propyl]-9-phenylphenanthridine diiodide.

* * * * *